(12) United States Patent
Xiao et al.

(10) Patent No.: US 7,759,488 B2
(45) Date of Patent: Jul. 20, 2010

(54) MONOAZOLE LIGAND PLATINUM ANALOGS

(75) Inventors: Zejun Xiao, San Antonio, TX (US); Harry Kochat, San Antonio, TX (US); Frederick H. Hausheer, Boerne, TX (US)

(73) Assignee: BioNumerik Pharmaceuticals, Inc., San Antonio, TX (US)

( * ) Notice: Subject to any disclaimer, the term of this patent is extended or adjusted under 35 U.S.C. 154(b) by 1161 days.

(21) Appl. No.: 11/340,805

(22) Filed: Jan. 26, 2006

(65) Prior Publication Data

US 2007/0004696 A1 Jan. 4, 2007

Related U.S. Application Data

(60) Provisional application No. 60/695,636, filed on Jun. 30, 2005.

(51) Int. Cl.
*C07F 15/00* (2006.01)
*A61K 31/555* (2006.01)
*A61P 31/00* (2006.01)
*A61P 35/00* (2006.01)

(52) U.S. Cl. ............ 546/2; 548/101; 514/184; 514/186

(58) Field of Classification Search ............... None
See application file for complete search history.

(56) References Cited

U.S. PATENT DOCUMENTS

| 4,921,963 A | * | 5/1990 | Skov et al. | ........... 548/101 |
| 5,624,919 A | * | 4/1997 | Farrell | ............... 514/184 |
| 6,894,049 B1 | * | 5/2005 | Wong et al. | ......... 514/252.1 |

FOREIGN PATENT DOCUMENTS

WO    WO 02/28871    *    4/2002

OTHER PUBLICATIONS

Bierbach et al., "Synthesis, Structure, Biological Activity, and DNA Binding of Platinum (II) Complexes of the Type trans-[PtCl2(NH3)L] (L = Planar Nitrogen Base). Effect of L and Cis/Trans isomerism on Sequence Specificity and Unwinding Properties Observed in Globally Platinated DNA", Inorganic Chemistry, 38(15), 3535-3542, 1999.*
Kasparkova et al., "DNA Binding by Antitumor trans-[PtCl2(NH3)(thiazole)]. Protein Recognition and Nucleotide Excision Repari of Monofunctional Adducts", Biochemistry, 42(3), 792-800, 2003.*
Muir et al., "Synthesis and Characterization of New Platinum (II) Complexes Containing Thiazole and Imidazole Donors", Chemical Abstracts, 108;215259, 1988.*
Wikipedia, definition of azole, downloaded Sep. 13, 2009.*
Raynaud, F. et al., "cis-Amminedichloro(2-methylpyridine) Platinum(II) (AMD473), a Novel Sterically Hindered Platinum Complex: In Vivo Activity, Toxicology, and Pharmacokinetics in Mice", Clinical Cancer Research, 3, 2063-2074, 1977.*
Yakovlev, K. I.. et al., "Mono- and Binuclear Platinum(II) Complexes with Benzotriazole", Chemical Abstracts, 126:25993, 1996.*
Uchiyama, et al., The Isolation, "Characterization, and Isomerization of cis- and trans-Bis(benzonitrile)dichloroplatinum(II)", Bull. Chem. Soc. Jpn., 54:181-85 (1981).

* cited by examiner

*Primary Examiner*—Fiona T Powers
(74) *Attorney, Agent, or Firm*—Scott A. Whitaker

(57) ABSTRACT

Disclosed herein are novel platinum-based analogs with a single substituted azole ligand: $RN=NR_7$, wherein the $RN=NR_7$ functional group is covalently bonded to the platinum through nitrogen of $NR_7$. The analogs also have nitrogen donor ligands capable of forming hydrogen bonds with the bases in DNA or RNA, and one or more leaving groups which can be displaced by water, hydroxide ions or other nucleophiles, which is thought to form active species in vivo, and then, form cross-linked complexes between nucleic acid strands, principally between purines in DNA (or RNA), i.e., at the Guanine or Adenine bases, thereof. These platinum analogs may also be more easily transported into tumor cells, due to their increased lipophilicity and are likely to be useful as anti-neoplastic agents, and in modulating or interfering with the synthesis or replication or transcription of DNA or translation or function of RNA in vitro or in vivo, as they are potentially capable of forming a platinum coordinate complex with an intact or nascent DNA or RNA and thereby interfering with cellular synthesis, transcription or replication of nucleic acid polynucleotides.

6 Claims, No Drawings

MONOAZOLE LIGAND PLATINUM ANALOGS

RELATED APPLICATIONS

The present application claims priority to Provisional Application Ser. No. 60/695,636, filed Jun. 30, 2005 and entitled: "AZOLE AND AZIDE LIGAND PLATINUM COMPOUNDS".

FIELD OF THE INVENTION

The present invention relates to novel platinum analogs possessing monoazole ligands and derivatives thereof, as well as methods for the synthesis of these aforementioned platinum complexes and derivatives thereof.

BACKGROUND OF THE INVENTION

The antineoplastic drug cisplatin (cis-diamminedichloroplatinum or "CDDP"), and related platinum based drugs including carboplatin and oxaliplatin™, are widely used in the treatment of a variety of malignancies, including, but not limited to, cancers of the ovary, lung, colon, bladder, germ cell tumors and head and neck. Platinum analogs are reported to act, in part, by aquation to form reactive aqua species, some of which may predominate intracellularly, and subsequently form DNA intrastrand coordination chelation cross-links with purine bases, thereby cross-linking DNA (predominantly intrastrand crosslinks between purine bases and less commonly as interstrand crosslinks between purine and pyrimidine bases) and disrupting the DNA structure and function, which is cytotoxic to cancer cells. Platinum-resistant cancer cells are resistant to the cytotoxic actions of these agents. Some cancers unpredictably exhibit intrinsic de novo natural resistance to the killing effects of platinum agents and undergo no apoptosis or necrosis or regression following initial platinum treatment. Other cancers exhibit varying degrees of cytotoxic sensitivity to platinum drugs, as evidenced by tumor regression following initial treatment, but subsequently develop an increasing level of platinum resistance which is manifested as an absence of tumor shrinkage or by frank tumor growth progression and/or metastases during or following treatment with the platinum drug (i.e., "acquired resistance"). New platinum agents are sought which can effectively kill tumor cells but that are also insensitive or less susceptible to tumor-mediated drug resistance mechanisms that are observed with other platinum agents.

In attempting to solve this problem, one research group (see, Uchiyama, et al., *Bull. Chem. Soc. Jpn.* 54:181-85 (1981)) has developed cisplatin analogues possessing a nitrile group substituted for each of the amine groups in cisplatin (IUPAC Nomenclature: cis-bisbenzonitriledichloroplatinum (II)). The structural formula for this analog is shown below:

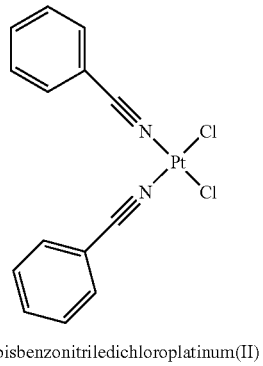

cis-bisbenzonitriledichloroplatinum(II)

In general, nitrile-ligand based platinum complexes are less polar and more lipophilic (i.e., hydrophobic) than the currently-marketed platinum-based drugs, and thus can be dissolved into less polar solvents including, but not limited to, methylene dichloride, chloroform, acetone, and the like. This greater lipophilicity may allow such analogs to be taken up more readily by cancer cells, by facile diffusion/transport through the lipid bilayer of the cell membrane, than current drugs. Thereby increasing the available concentration of the platinum species that can participate in cytotoxic anti-tumor effects on the DNA within cancer cells.

Additionally, the lone pair of electrons on nitrogen in the nitrile group is located in the sp hybrid orbital, which is closer to the nitrogen nucleus than the $sp^3$ hybrid orbital in the amine ligand. Thus, in platinum analogs, the attraction of the nitrogen nucleus in nitrile ligand for the lone pair of sharing electrons with platinum is greater than in the ammine ligand. This effect results in decreasing the ionic effect between platinum (II) and the leaving group, and increasing the covalent bonding. As a result, the leaving groups are more difficulty to displace by substitution, including aquation, and therefore slower rates of aquation are observed in nitrile N-donor platinum complexes as compared to ammine platinum complexes. It would seem that both the nitrile ligand-based platinum complexes and the intermediates they form upon hydrolysis, possess a slower rate of reaction with naked DNA compared to ammine ligand-based platinum complexes. It is assumed that the slower rate of cross-linkage formation of platinum analogs with DNA bases may be less susceptible to tumor-mediated platinum-DNA repair mechanisms, which is one of the key platinum drug resistance mechanisms. In addition, and equally important from a pharmacological, toxicological, chemical and drug-resistance circumvention mechanistic points of view, the nitrile-, azido- and R—N=N-containing platinum complexes described below are predicted to be substantially less chemically reactive than cisplatin, carboplatin and oxaliplatin. Therefore, these nitrile-, azido- and R—N=N-containing platinum complexes react substantially more slowly with, and thereby avoid unwanted platinum-sulfur and platinum-nitrogen conjugates with, the thiols, disulfides and proteins/peptides present in vivo; specifically the sulfur-containing physiological thiols, disulfides and peptides/amino acids, including but not limited to, glutathione, cysteine, homocysteine, methionine and all other sulfur-containing and imidazole-containing (e.g., histidine), or arginine or lysine di- tri- and larger peptides, that participate in tumor-mediated platinum drug resistance. Therefore, these novel nitrile, azido and other nitrogen ligand-based platinum complexes have potential to circumvent de novo and acquired tumor-mediated cisplatin resistance and kill cancer cells with natural resistance to known platinum drugs. The platinum complexes described below are also thought to permit controlled reduction of the chemical reactivity of the platinum species to such a degree that greater amounts of the platinum species are also delivered intracellularly. This improved delivery of platinum that is available for intracellular DNA adduct formation is mediated by substantial reduction in the amount of non-effective and non-specific reactions of these novel platinum species with proteins and physiological thiols and disulfides, which can attenuate the antitumor effects of conventional platinum analogs.

The same advantages are possessed by cisplatin analogs where one ammine group in cisplatin is replaced with an azole ligand. These analogs would be capable of hydrogen or electrostatic bonding with DNA. The presumed advantage is that these platinum complexes involve a slower and more controlled reduction of the chemical reactivity of the platinum species to such a degree that greater amounts of the platinum species are delivered intracellularly. This improved delivery of platinum that is available for intracellular DNA adduct formation is mediated by substantial reduction in the amount of non-effective and non-specific reactions of these novel platinum species with proteins and physiological thiols and disulfides (especially glutathione, which is present in large concentrations intracellularly), which can otherwise attenuate the antitumor effects of conventional platinum analogs.

The reaction for cisplatin hydrolysis is illustrated below in Scheme I:

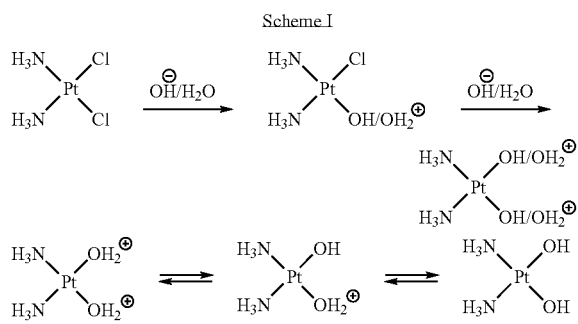

Cisplatin is relatively stable in human plasma, where a high concentration of chloride prevents aquation of cisplatin. Once cisplatin enters a tumor cell, where a much lower concentration of chloride exists, one or both of the chloride ligands of cisplatin is displaced by water to form an aqua active intermediate form (as illustrated above), which in turn can react rapidly with DNA purines to form stable platinum—purine DNA adducts. Another unwanted side reaction of such platinum species is side reactions with physiological thiols and disulfides as well as proteins; such reactions are thought to not be beneficial in killing tumor cells.

Therefore, the development of platinum analogs that do not react as readily with physiological thiols/disulfides and proteins may be markedly more effective against drug-resistant tumors than either cisplatin or the currently utilized analogs.

SUMMARY OF THE INVENTION

The inventions described and claimed herein have many attributes and embodiments including, but not limited to, those set forth or described or referenced in this Brief Summary. It is not intended to be all-inclusive and the inventions described and claimed herein are not limited to or by the features or embodiments identified in this Brief Summary, which is included for purposes of illustration only and not restriction.

Disclosed herein are novel platinum-based analogs with a substituted azole ligand: $RN=NR_7$; wherein the $RN=NR_7$ functional group is covalently bonded to the platinum, and R and $R_7$ substitute may tether to form heterocyclic ring or aromatic ring system containing nitrogen-to-nitrogen bonding. These analogs also have nitrogen donor ligands capable of forming hydrogen bonds with the bases in DNA or RNA, and one or more leaving groups which can be displaced by water, hydroxide ions or other nucleophiles, which is thought to form active species in vivo, and then, form cross-linked complexes between nucleic acid strands, principally between purines in DNA (or RNA), i.e., at the Guanine or Adenine bases thereof. The reaction scheme for hydrolysis of the leaving groups in these novel platinum-based analogs would be analogous to that shown above for cisplatin, where the intermediates at the leaving group sites include $OH/OH_2^+$; $OH_2^+$ and OH.

Unlike bis-nitrile platinum analogs, monoazole platinum analogs retain the ammine donor ligand, which is thought to provide a strong hydrogen bonding capability in the area close to the platinum nucleus. These platinum analogs may also be more easily transported into tumor cells, due to their increased lipophilicity. Hence, these novel analogs are likely to be useful as anti-neoplastic agents, and in modulating or interfering with the synthesis or replication or transcription of DNA or translation or function of RNA in vitro or in vivo, as they are potentially capable of forming a platinum coordinate complex with an intact or nascent DNA or RNA and thereby interfering with cellular synthesis, transcription or replication of nucleic acid polynucleotides.

In the platinum-based analogs of the present invention, either one or both of the leaving groups, which are hydrolyzed in the intracellular environment to generate, first hydroxyl groups at the leaving group positions, and then produce water, leaving the molecule labile and suitable for nucleophilic substitution. Platinum is capable of rapidly chelating and cross-linking with oligonucleotides through reaction with the Guanine or Adenine base of a DNA (or possibly also an RNA) oligonucleotide. This cross-linking functions to inhibit or prevent further oligonucleotide chain extension.

Cisplatin is relatively stable in human plasma, where a high concentration of chloride prevents aquation of cisplatin. However, once cisplatin enters a tumor cell, where a much lower concentration of chloride exists, one or both of the chloride ligands of cisplatin is displaced by water to form an aqua-active intermediate form (as shown above), which in turn can react rapidly with DNA purines (i.e., A and G) to form stable platinum—purine—DNA adducts. One limitation associated with the bis-nitrile platinum complexes is that their DNA adducts may not be as stable as cisplatin-DNA adducts, because the ammine groups in cisplatin participate in local hydrogen bonding with the DNA structure to stabilize these DNA-platinum complexes. The lack of local hydrogen bonding interaction between the bis-nitrile platinum analogs and the DNA structure potentially decreases the binding affinity of bis-nitrile platinum complexes with DNA.

Thus, there remains a need for new, novel platinum analogs that: (i) can form more stable complexes (with increased binding affinity) and (ii) do not react as readily in unwanted side-reactions with physiological thiols/disulfides and proteins.

DETAILED DESCRIPTION OF THE INVENTION

The preferred embodiments herein described are not intended to be exhaustive, or to limit the invention to the precise forms disclosed. They are chosen and described to best illustrate the principles of the invention, and its application and practical use to best enable others skilled in the art to follow its teachings.

Definitions

All definitions provided by: *Hawley's Condensed Chemical Dictionary*, 14th Edition, John Wiley & Sons, Inc., Publishers ((2001) and *American Hospital Formulary Service, Drug Information*, American Society of Health-System Pharmacists, Publishers (1999).

"Scaffold" means the fixed structural part of the molecule of the formula given.

"Fragments", "Moieties" or "Substituent Groups" are the variable parts of the molecule, designated in the formula by variable symbols, such as $R_x$, X or other symbols. Fragments may consist of one or more of the following:

"$C_x$-$C_y$ alkyl" generally means a straight or branched-chain aliphatic hydrocarbon containing as few as x and as many as y carbon atoms. Examples include "$C_1$-$C_6$ alkyl" (also referred to as "lower alkyl"), which includes a straight or branched chain hydrocarbon with no more than 6 total carbon atoms, and $C_1$-$C_{16}$ alkyl, which includes a hydrocarbon with as few as one up to as many as sixteen total carbon atoms, and the like. In the present application, the term "alkyl" is defined as comprising a straight or branched chain hydrocarbon of between 1 and 20 atoms, which can be saturated or unsaturated, and may include heteroatoms such as nitrogen, sulfur, and oxygen;

"$C_x$-$C_y$ alkylene" means a bridging moiety formed of as few as "x" and as many as "y" —$CH_2$— groups. In the present invention, the term "alkylene" is defined as comprising a bridging hydrocarbon having from 1 to 6 total carbon atoms which is bonded at its terminal carbons to two other atoms (—$CH_2$—)$_x$ where x is 1 to 6;

"$C_x$-$C_y$ alkenyl or alkynyl" means a straight or branched chain hydrocarbon with at least one double bond(alkenyl) or triple bond (alkynyl) between two of the carbon atoms;

"$C_x$-$C_y$ alkoxy" means a straight or branched hydrocarbon chain with as few as x and as many as y carbon atoms, with the chain bonded to the scaffold through an oxygen atom;

"Alkoxycarbonyl" (aryloxycarbonyl) means an alkoxy (aryloxy) moiety bonded to the scaffold through a carbonyl;

"Halogen" or "Halo" means chloro, fluoro, bromo or iodo;

"Acyl" means —C(O)—R, where R is hydrogen, $C_x$-$C_y$ alkyl, aryl, $C_x$-$C_y$ alkenyl, $C_x$-$C_y$ alkynyl, and the like;

"Acyloxy" means —O—C(O)—R, where R is hydrogen, $C_x$-$C_y$ alkyl, aryl, and the like;

"$C_x$-$C_y$ Cycloalkyl" means a hydrocarbon ring or ring system consisting of one or more rings, fused or unfused, wherein at least one of the ring bonds is completely saturated, with the ring(s) having from x to y total carbon atoms;

"Aryl" generally means an aromatic ring or ring system consisting of one or more rings, preferably one to three rings, fused or unfused, with the ring atoms consisting entirely of carbon atoms. In the present invention, the term "aryl" is defined as comprising as an aromatic ring system, either fused or unfused, preferably from one to three total rings, with the ring elements consisting entirely of 5-8 carbon atoms;

"Arylalkyl" means an aryl moiety as defined above, bonded to the scaffold through an alkyl moiety (the attachment chain);

"Arylalkenyl" and "Arylalkynyl" mean the same as "Arylalkyl", but including one or more double or triple bonds in the attachment chain;

"Amine" means a class of organic analogs of nitrogen that may be considered as derived from ammonia ($NH_3$) by replacing one or more of the hydrogen atoms with alkyl groups. The amine is primary, secondary or tertiary, depending upon whether one, two or three of the hydrogen atoms are replaced. A "short chain anime" is one in which the alkyl group contain from 1 to 10 carbon atoms;

"Ammine" means a coordination analog formed by the union of ammonia with a metallic substance in such a way that the nitrogen atoms are linked directly to the metal. It should be noted the difference from amines, in which the nitrogen is attached directly to the carbon atom;

"Azide" means any group of analogs having the characteristic formula $R(N_3)_x$. R may be almost any metal atom, a hydrogen atom, a halogen atom, the ammonium radical, a complex [CO(NH$_3$)$_6$], [Hg(CN)$_2$M], (with M=Cu, Zn, Co, Ni) an organic radical like methyl, phenyl, nitrophenol, dinitrophenol, p-nitrobenzyl, ethyl nitrate, and the like. The azide group possesses a chain structure rather than a ring structure;

"Imine" means a class of nitrogen-containing analogs possessing a carbon-to-nitrogen double bond (i.e., R—CH=NH); and "Heterocycle" means a cyclic moiety of one or more rings, preferably one to three rings, fused or unfused, wherein at least one atom of one of the rings is a non-carbon atom. Preferred heteroatoms include oxygen, nitrogen and sulfur, or any combination of two or more of those atoms. The term "Heterocycle" includes furanyl, pyranyl, thionyl, pyrrolyl, pyrrolidinyl, prolinyl, pyridinyl, pyrazolyl, imidazolyl, triazolyl, tetrazolyl, oxathiazolyl, dithiolyl, oxazolyl, isoxazolyl, oxadiazolyl, pyridazinyl, pyrimidinyl, pyrazinyl, piperazinyl, oxazinyl, thiazolyl, and the like.

"Substituted" modifies the identified fragments (moieties) by replacing any, some or all of the hydrogen atoms with a moiety (moieties) as identified in the specification. Substitutions for hydrogen atoms to form substituted analogs include halo, alkyl, nitro, amino (also N-substituted, and N,N di-substituted amino), sulfonyl, hydroxy, alkoxy, phenyl, phenoxy, benzyl, benzoxy, benzoyl, and trifluoromethyl.

The term "antineoplastic agent" or "chemotherapeutic agent" refers to an agent that inhibits, prevents, or stops the growth or metastases of neoplasms, or kills neoplastic cells directly by necrosis, or by apoptosis of neoplasms.

As defined in the present invention, an "effective amount" or a "pharmaceutically-effective amount" in reference to the compounds or compositions of the instant invention refers to the amount sufficient to induce a desired biological, pharmacological, or therapeutic outcome in a subject with neoplastic disease. That result can be prevention, mitigation, reduction in severity, shortening the time to resolution or alleviation of the signs, symptoms, or exert a medically-beneficial effect upon the underlying pathophysiology or pathogenesis of an expected or observed side-effect, toxicity, disorder or condition, or any other desired alteration of a biological system. In the present invention, the result will generally include the prevention, delay, mitigation, decrease, or reversal of chemotherapeutic agent-associated toxicity, and an increase in the frequency, number or treatments and/or duration of chemotherapeutic therapy.

As used herein, "preventing" means preventing the onset, or the development of greater severity in an adverse sign or condition in a subject, in whole or in-part, or ameliorating or controlling such adverse sign or condition in the subject, as they involve any such chemotherapeutic agent-associated adverse side effect.

Disclosed herein are novel platinum-based analogs with one substituted azole ligand: $RN=NR_7$, wherein the $RN=NR_7$ functional group is covalently bonded to the platinum, and R and $R_7$ substitute may tether to form heterocyclic ring or aromatic ring system containing nitrogen-to-nitrogen bonding. These analogs also have nitrogen donor ligands capable of forming hydrogen bonds with the bases in DNA or RNA, and one or more leaving groups which can be displaced by water, hydroxide ions or other nucleophiles, which is thought to form active species in vivo, and then, form cross-linked complexes between nucleic acid strands, principally between purines in DNA (or RNA), i.e., at the Guanine or Adenine bases thereof. The reaction scheme for hydrolysis of the leaving groups in these novel platinum-based analogs would be analogous to that shown above for cisplatin, where the intermediates at the leaving group sites include $OH/OH_2^+$; $OH_2^+$ and $OH$.

Unlike bis-nitrile platinum analogs, monoazole ligand cisplatin analogs retain the ammine donor ligand, which is thought to provide a strong hydrogen bonding capability in the area close to the platinum nucleus. These platinum analogs may also be more easily transported into tumor cells, due to their increased lipophilicity. Hence, these novel analogs are likely to be useful as anti-neoplastic agents, and in modulating or interfering with the synthesis or replication or transcription of DNA or translation or function of RNA in vitro or in vivo, as they are potentially capable of forming a platinum coordinate complex with an intact or nascent DNA or RNA and thereby interfering with cellular synthesis, transcription or replication of nucleic acids polynucleotides.

These novel platinum-based analogs include the following structural formulas (A, B and C):

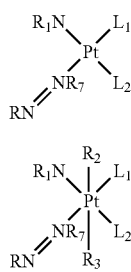

-continued

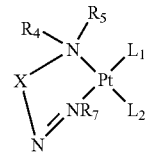

In these aforementioned platinum-based analogs, either one or both of the leaving groups (i.e., $L_1$ and $L_2$) are hydrolyzed in the intracellular environment to generate: initially, hydroxyl groups at the leaving group position(s), and then, subsequently, produce water, leaving the molecule labile and suitable for nucleophilic substitution. In the platinum-based analogs of the present invention, either one or both of the leaving groups, which are hydrolyzed in the intracellular environment to generate, first hydroxyl groups at the leaving group positions, and then produce water, leaving the molecule labile and suitable for nucleophilic substitution. Platinum is capable of rapidly chelating and cross-linking with oligonucleotides through reaction with a Guanine or Adenine base of a DNA (or possibly also an RNA) oligonucleotide. The platinum cross-links the oligonucleotide at the 7-position of the Guanine or Adenine moiety. This cross-linking functions to inhibit or prevent further oligonucleotide chain extension.

Examples of suitable $L_1$ and $L_2$ moieties include, but are not limited to, carboxylate, alkoxyl, hydroxyl, water, peroxide, sulfur, disulfide, sulfoxide, chloride, bromide, fluoride, iodide, amine, pyridine, pyrrole, furan, thiofuran, chlorate, nitrate, nitrite, sulfate, sulfite, alkyl phosphonate, alkylphosphonate, phosphorothiolate, alkylphosphorothiolate, phosphoramide, alkyl phosphoramide, phosphate, phosphite, phosphide, phosphine, thio phosphonate, alkyl phosphoramidates, phosphoramidates, aryl phosponates and carbocyclic phosponates. It should be noted that, in general, $L_1$ and $L_2$ should both be leaving groups, but the complexes described herein are often capable of forming complexes with nucleic acids even if only one of $L_1$ and $L_2$ is a leaving group.

The N group within the R, $R_1$, $R_4$, $R_5$, $R_7$ substituent groups in the platinum-based analogs of the present invention are typically carrier ligands which may include, but are not limited to, primary, secondary or tertiary amine groups, pyridine, azole, azide, cyclic azole, cyclic azide, pyrrole, pyrazole or imidazole; wherein, the $R_1$, $R_4$, $R_5$ may include, but are not limited to, hydrogen, alkyl, cycloalkyl, aryl, acetate, alkyl or cycloalkyl. At least one of carrier ligands is an azole or azide. The carrier ligands should be charge neutral in the complex, and the carrier ligands and the R and $R_7$ group (which include, but are not limited to, alkyl, cycloalkyl, aryl, acetate or another suitable functional group) should not be so large as to cause spatial or steric interference with DNA chelation. It should also be noted that the R and $R_7$ groups may bond together, thus forming a cyclic azole. As noted above, amine groups in the carrier ligand position can participate in hydrogen bonding, which can help stabilize the DNA adducts.

Illustrated below, in Scheme II, is the monoazole ligand-containing platinum analogs disclosed herein forming an adduct with a DNA base. Referring to this reaction scheme, presumably a nucleophilic hydroxyl group initially substitutes for chloro to form the monoaqua species (2). Monoaqua intermediates readily react with the DNA base (G/A) to form DNA adducts (3). The adduct (3) can further hydrolyze to the monoaqua species (4) to form the adduct (5), which results in the anti-neoplastic effect.

Scheme II

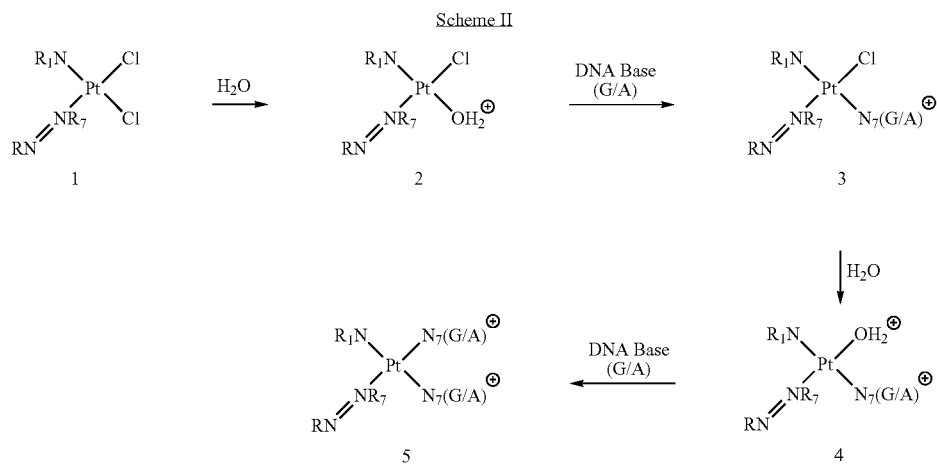

Specific Examples of Synthesis of Platinum Analogs

I. Proposed Procedure for Preparation of cis-amminedichloro [1-(phenylsulfonyl)-1H-benzotriazole] platinum(II)

To a solution of K[PtNH$_3$Cl$_3$] (150 mg) in 4 mL of deionized water is added 0.1 g of 1-(phenylsulfonyl)-1H-benzotriazole. The resulting mixture is stirred under heated conditions for 24 hours. The pale yellow precipitate was filtered, washed with deionized water and ethyl ether, and dried under high vacuum to give a crude product. Recrystallization from ethyl alcohol afforded a pure product.

II. Proposed Procedure for Preparation of cis-amminedichloro [5-phenyl-1H-tetrazole] platinum(II)

To a solution of K[PtNH$_3$Cl$_3$] (150 mg) in 4 mL of deionized water is added 0.1 g of 5-phenyl-1H-tetrazole. The resulting mixture is stirred under heated conditions for 24 hours. The pale yellow precipitate was filtered, washed with deionized water and ethyl ether, and dried under high vacuum to give a crude product. Recrystallization from ethyl alcohol afforded a pure product.

III. Proposed Procedure for Preparation of cis-amminedichloro [1-[(phenylthio)methyl]-1H-benzotriazole] platinum(II)

To a solution of K[PtNH$_3$Cl$_3$] (150 mg) in 4 mL of deionized water was added 0.1 g of 1-[(phenylthio)methyl]-1H-benzotriazole. The resulting mixture is stirred under heated conditions for 24 hours. The pale yellow precipitate was filtered, washed with deionized water and ethyl ether, and dried under high vacuum to give a crude product. Recrystallization from ethyl alcohol afforded a pure product.

IV. Proposed Procedure for Preparation of cis-amminedichloro phthalazineplatinum(II)

To a solution of K[PtNH$_3$Cl$_3$] (150 mg) in 4 mL of deionized water is added 0.1 g of phthalazine. The resulting mixture is stirred under heated conditions for 24 hours. The pale yellow precipitate was filtered, washed with deionized water and ethyl ether, and dried under high vacuum to give a crude product. Recrystallization from ethyl alcohol afforded a pure product.

V. Proposed Procedure for Preparation of cis-amminedichloro [1(2H)-phthalazineone] platinum(II)

To a solution of K[PtNH$_3$Cl$_3$] (150 mg) in 4 mL of deionized water is added 0.1 g of 1(2H)-phthalazineone. The resulting mixture is stirred at 23° C. for 24 hours. The pale yellow precipitate was filtered, washed with deionized water and ethyl ether, and dried under high vacuum to give a crude product. Recrystallization from ethyl alcohol afforded a pure product.

VI. Proposed Procedure for Preparation of cis-amminedichloro [1(2H)-phthalhydrazide] platinum(II)

To a solution of K[PtNH$_3$Cl$_3$] (150 mg) in 4 mL of deionized water is added 0.1 g of 1(2H)-phthalhydrazide. The resulting mixture is stirred under heated conditions for 24 hours. The pale yellow precipitate was filtered, washed with deionized water and ethyl ether, and dried under high vacuum to give a crude product. Recrystallization from ethyl alcohol afforded a pure product.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising ", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The present invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and applicants reserve the right to revise the application or claims to refer specifically to any individual member or any subgroup of members of the Markush group.

Other embodiments are within the following claims. The patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

What is claimed is:

1. A platinum-containing analog, wherein said analog is cis-amminedichloro [1-(phenylsulfonyl)-1H-benzotriazole] platinum(II).

2. A platinum-containing analog, wherein said analog is cis-amminedichloro [5-phenyl-1H-tetrazole] platinum(II).

3. A platinum-containing analog, wherein said analog is cis-amminedichloro [1-[(phenylthio)methyl]-1H-benzotriazole] platinum(II).

4. A platinum-containing analog, wherein said analog is cis-amminedichloro phthalazineplatinum(II).

5. A platinum-containing analog, wherein said analog is cis-amminedichloro [1(2H)-phthalazineone] platinum(II).

6. A platinum-containing analog, wherein said analog is cis-amminedichloro [1(2H)-phthalhydrazide] platinum(II) diamino.

* * * * *